United States Patent
Hoyt (10) Patent No.: US 6,674,527 B2
(45) Date of Patent: Jan. 6, 2004

(54) RATIOMETRIC BACKGROUND CORRECTION FOR FLUORESCENCE POLARIZATION ASSAYS

(75) Inventor: Clifford C. Hoyt, Needham, MA (US)

(73) Assignee: Cambridge Research & Instrumentation Inc., Woburn, MA (US)

( * ) Notice: Subject to any disclaimer, the term of this patent is extended or adjusted under 35 U.S.C. 154(b) by 106 days.

(21) Appl. No.: 10/085,775

(22) Filed: Feb. 27, 2002

(65) Prior Publication Data

US 2002/0159056 A1 Oct. 31, 2002

Related U.S. Application Data

(60) Provisional application No. 60/271,790, filed on Feb. 27, 2001.

(51) Int. Cl.$^7$ .............................. G01J 3/30; G01N 21/64
(52) U.S. Cl. .................... 356/317; 356/307; 250/459.1; 250/461.2
(58) Field of Search ................................. 356/317, 307; 250/458.1–461.2; 436/546, 172

(56) References Cited

U.S. PATENT DOCUMENTS 5,166,052 A * 11/1992 Cercek et al. ........... 250/458.1
6,066,505 A * 5/2000 Cheng et al. ............... 436/546
6,566,143 B2 * 5/2003 Hoyt ........................... 356/317
2001/0046673 A1 * 11/2001 French et al. ................... 435/6

OTHER PUBLICATIONS

Journal of Biomolecular Screening, vol. 5, No. 5, 2000, "Fluorescence Polarization and Anisotropy in High Throughput Screening: Perspective and Primer", John C. Owicki.

* cited by examiner

Primary Examiner—Zandra V. Smith
Assistant Examiner—Kara Geisel
(74) Attorney, Agent, or Firm—Cohen, Pontani, Lieberman & Pavane (57) ABSTRACT

A method in which a multiplicative ratio approach is used to remove the effects of the unwanted background fluorescence when making fluoroescence polarization (FP) measurements rather than the conventional subtractive approach, thus preserving both the precision and accuracy of the FP measurements, is disclosed. The method comprises selecting an appropriate multiplicative ratio, then calculating the selected multiplicative ratio using sample measurements. The calculated multiplicative ratio is multiplied by an appropriate value in a standard FP measurement equation or an appropriate value in an equation derived from a standard FP measurement equation. After this, the corrected FP measurement is calculated. When such multiplicative ratios are applied to the appropriate value or values in an FP measurement equation, the effects of background noise can be reduced without decreasing the precision of the FP measurements.

19 Claims, 5 Drawing Sheets

RATIOMETRIC BACKGROUND CORRECTION FOR FLUORESCENCE POLARIZATION ASSAYS

RELATED APPLICATIONS

This application claims priority from U.S. Provisional Patent Application Ser. No. 60/271,790 which was filed on Feb. 27, 2001 and which is hereby incorporated by reference.

BACKGROUND OF THE INVENTION

1. Field of the Invention

This application relates generally to fluorescence polarization measurements and, in particular, to a method of correcting fluorescence polarization measurements for the effects of background noise.

2. Description of the Related Art

Fluorescence polarization (FP) measurements are used to detect molecular interaction, since molecular interaction typically leads to an increase in the polarization signal. See John C. Owicki, "Fluorescence Polarization and Anisotrophy in High Throughput Screening: Perspectives and Primer", JOURNAL OF BIOMOLECULAR SCREENING, Vol. 5, No. 5, 2000 (Hereinafter referred to as *"FP/FA Primer"*, and incorporated by reference) for various examples of assays using fluorescence polarization.

Figure 1:
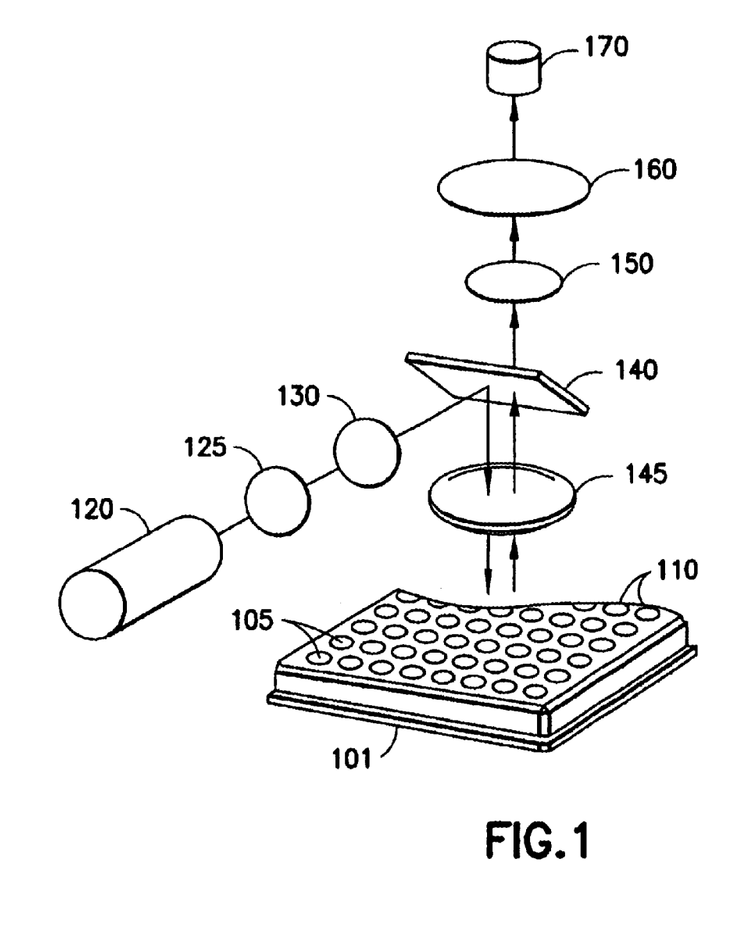
FIG. 1 is a conventional Fluorescence Polarization Plate Reader.

FIG. 1 shows a conventional FP Plate Reader which is used for taking FP measurements from samples in a microtitre plate. Plate 101 contains Samples 105 in Wells 110. Samples 105 are typically comprised of a cell preparation, buffers, a drug or other target substance being tested, and fluorophores that will fluoresce when excited by light. This excitation light is emitted by Lamp 120, filtered by Filter 125, and polarized by Excitation Polarizer 130, before reflecting off of Dichroic Beamsplitter 140 through Objective 145 onto Samples 105. The light emitted by the fluorophores in Samples 105 will proceed through Objective 145 and Dichroic Beamsplitter 140, before being filtered by Filter 150 and analyzed by Emission Polarizer 160. The analyzed emitted light is then detected by Detector 170.

The conventional equation for calculating FP takes the difference between the measured signals when the polarizers are parallel (i.e., when Excitation Polarizer 130 lets light through with the same polarization as light let through Emission Polarizer 160) and when the polarizers are perpendicular (i.e., when Excitation Polarizer 130 lets light through with a polarization orthogonal to the light let through Emission Polarizer 160), and divides this C difference by the sum of the two measurements, as shown by:

$$FP = 1000 * \frac{I_{\parallel} - I_{\perp}}{I_{\parallel} + I_{\perp}} \quad \text{(Equation 1)}$$

where $I_{\parallel}$ is the intensity measurement with the polarizers parallel, and $I_{\perp}$ is the intensity measurement with the polarizers perpendicular. The FP signal is a unitless number that indicates degree of fluorescence polarization (DOP), and is typically called millipolarization, "milliP" or "mP".

It is the difference $(I_{\parallel} - I_{\perp})$ that carries the assay information, the remaining terms in the equation are for normalization. The object of detection of FP measurements, successful molecular binding events, are indicated by typically small variations in the difference $(I_{\parallel} - I_{\perp})$. Because of the need for detecting these small variations, the utility of instruments designed for FP measurement is primarily dependent on the precision of the instrument, and secondarily on the accuracy. In other words, it is more important that the intensity measurements $I_{\parallel}$ and $I_{\perp}$ are precise relative to each other rather than they be individually absolutely accurate.

When making conventional FP measurements using conventional FP measurement devices, one must often choose between accuracy and precision. As an example, consider the problem of background fluorescence in a conventional FP Plate Reader. Background fluorescence is caused by non-probe or non-subject (the subject being the molecule under study) elements, such as Wells 110 or the cell preparation and buffers in Samples 105, which fluoresce and add to the emitted light which reaches Detector 170. This can affect the accuracy of the FP measurements. The accuracy problem can be illustrated by the following hypothetical situation, where a "pure" FP measurement (meaning "purely" from the fluorophores or probes) is sought:

$$FP_{probe} = 1000 * \frac{I_{\parallel}^{probe} - I_{\perp}^{probe}}{I_{\parallel}^{probe} + I_{\perp}^{probe}} \quad \text{(Equation 2)}$$

where
$I_{\parallel}^{probe}$=the intensity signal of parallel polarized light from the probes; and
$I_{\perp}^{probe}$=the intensity signal of perpendicularly polarized light from the probes.

In our hypothetical, we will assume that $I_{\parallel}^{probe}$=60,000 and $I_{\perp}^{probe}$=40,000, so the actual FP of the probes, $FP_{probe}$,=200 mP. Furthermore, we will assume that the intensity signal of the background is equal to some proportion of the total intensity signal of the probes:

$$I^{bkgrnd} = I^{bkgrnd::probe} * I^{probe}$$

where
$I^{bkgrnd}$=total intensity signal of the background;
$I^{bkgrnd::probe}$=the ratio of background signal to probe signal; and
$I^{probe}$=total intensity signal of the probes.

A reasonable assumed value for $I^{bkgrnd::probe}$ is ⅓ or 0.33, which will result in $I^{bkgrnd}$=33,000. Now, we will determine the parallel and perpendicularly polarized components of the background signal:

$$I_{\parallel}^{bkgrnd} = I^{bkgrnd} * \frac{(1 + FP_{bkgrnd})}{2000}$$

$$I_{\perp}^{bkgrnd} = I^{bkgrnd} - I_{\parallel}^{bkgrnd}$$

where
$I_{\parallel}^{bkgrnd}$=the intensity of the parallel polarized component of the background;
$FP_{bkgrnd}$=the fluorescence polarization of the background; and
$I_{\perp}^{bkgrnd}$=the intensity of the perpendicularly polarized component of the background.

Assuming a value of 450 mP for the background FP ($FP_{bkgrnd}$), the parallel polarized component of the background, $I_{\parallel}^{bkgrnd}$, equals 23,930 and the perpendicularly polarized component, $I_{\perp}^{bkgrnd}$, equals 9075. The total intensity of the polarized signal received by Detector 170 equals the combination of the probe signal and the background signal:

$$I_\perp^{meas} = I_\perp^{bkgrnd} + I_\perp^{probe}$$

$$I_\perp^{meas} = 83,930$$

$$I_\parallel^{meas} = I_\parallel^{bkgrnd} + I_\parallel^{probe}$$

$$I_\parallel^{meas} = 9075$$

In the end, the final measured FP as calculated by the intensity measurements at the detector is:

$$FP_{meas} = 1000 * \frac{I_\parallel^{meas} - I_\perp^{meas}}{I_\parallel^{meas} + I_\perp^{meas}} \quad \text{(Equation 3)}$$

$$FP_{meas} = 262$$

Thus, the measured FP of 262 is more than 25% in error (from the real FP of 200). If this type of error margin is unacceptable to the experimenter, she may use a method to compensate for the signal noise generated by the background. Such methods have been developed over time, as discussed in FP/FA Primer. These conventional methods to compensate for background fluorescence use a subtractive approach to decrease the background signal source. For example, Equation 4 below directly subtracts parallel and perpendicular measurements of background wells (containing one or more assay components, but not the fluorophore) from the parallel and perpendicular measurements of the sample wells under study (all assay materials including fluorophore):

$$FP_{meas} = 1000 * \frac{(I_\parallel^{meas} - I_\parallel^{bkgrnd}) - (I_\perp^{meas} - I_\perp^{bkgrnd})}{(I_\parallel^{meas} - I_\parallel^{bkgrnd}) + (I_\perp^{meas} - I_\perp^{bkgrnd})} \quad \text{(Equation 4)}$$

The disadvantage of this approach is that the accuracy of background correction is subject to changes in excitation lamp intensity, well-to-well variations in sampled volume and meniscus, and the degree of photobleaching between the background measurement and the sample measurement. In effect, the background correction step injects into the calculation additional noise, which reduces measurement precision. Thus, in order to achieve greater accuracy in one's FP measurements, one may end up sacrificing the precision of such measurements. But, as is discussed above, this is not desirable, since the precision of these measurements relative to each other is more important than the accuracy of the individual measurements.

Some experimenters may prefer losing the accuracy of their measurements, i.e., by not performing any background compensation, in order to save the precision of the measurements. However, this solution (of not performing any background correction) is also not desirable because of the effects of such a loss of accuracy when making comparisons between different experiments, assays, samples, etc. For example, part of the job of assay development technicians is to compare assays from different experiments; but this is made more difficult (and the results are more questionable) when the accuracy of the measurements from the different experiments is problematic.

A particularly problematic situation is when the background signal is a substantial portion of the total signal, say 25% or more. This typically occurs when tracer concentrations are reduced to less than a few hundred picoMolar (pM). For example, if a) the effective sampled volumes vary from well to well by 5%,
b) 25% of the measured fluorescence emission signal is background fluorescence,
c) the background FP signal is 450 mP, and
d) the actual sample FP signal is 150 mP, the degradation of the instrument measurement, as represented by standard deviations in multiple FP measurements, due to background compensation alone would be 5 mP. This limitation may be the most significant barrier to performing assays with tracer concentrations less than 100 pM. When dealing with such small amounts, not using any background compensation is also unsatisfactory, because the effect of the background noise becomes so large in comparison to the real (probe) signal that both the precision and accuracy of the FP measurements are substantially degraded. This is a crucial problem because many assays should be operated at such low levels, near the $K_d$ point.

Thus, there is a need for a background correction scheme that does not add noise into the FP measurement calculation, and that enables background-corrected measurement with the measurement of the actual sample providing the only source of noise. Furthermore, there is a need for a more precise method of correcting FP measurements for the effects of background fluorescence, where the background fluorescence correction does not inject the noise or uncertainty of the conventional method into the FP measurement. This need is particularly acute when fluorophore concentrations get low (e.g., below a few hundred pM), which causes significant error in both the precision and accuracy of FP measurements in the conventional method.

SUMMARY OF THE INVENTION

One object of the present invention is to provide a background correction scheme that does not add noise into the FP measurement calculation, and that enables background-corrected measurement with the measurement of the actual sample providing the only source of noise.

Another object of the present invention is to provide a more precise method of correcting FP measurements for the effects of background fluorescence, where the background fluorescence correction does not inject the noise or uncertainty of the conventional method into the FP measurement.

Yet another object of the present invention is to provide a correction method which does not introduce a significant source of error when fluorophore concentrations get low (e.g., below a few hundred pM).

Yet another object of the present invention is to provide a method which confers greater precision and accuracy on FP measurements than conventional methods when fluorophore concentrations get low (e.g., below a few hundred pM).

Still another object of the present invention is to provide more accurate fluorescence polarization measurements without necessarily degrading the instrument signal-to-noise ratio.

These and other objects are achieved by the present invention in which a multiplicative ratio approach is used to remove the effects of the unwanted background fluorescence rather than the conventional subtractive approach, thus preserving both the precision and accuracy of the FP measurements. The method according to the present invention, comprises selecting an appropriate multiplicative ratio is selected, then the selected multiplicative ratio is calculated using measurements from samples. The calculated multiplicative ratio is multiplied by an appropriate value in one of the standard FP measurement equations (Equations 1 or 4) or an appropriate value in an equation derived from one of the standard FP measurement equations. After (or during) this calculation, the corrected FP measurement is calculated. When such multiplicative ratios are applied to the appropriate value or values in an FP measurement equation, the effects of background noise can be reduced without decreasing the precision of the FP measurements.

In a first presently preferred embodiment of the present invention, a multiplicative ratio comprised of the relative proportion of light from a background well fluorescence emission to light from a sample well fluorescence emission is calculated, and is appropriately multiplied into the fluorescence polarization calculation, resulting in a corrected FP measurement that is both accurate and precise. In a second presently preferred embodiment, a multiplicative ratio comprised of the total intensity of the first sample divided by the total intensity of the current sample is calculated, and is appropriately multiplied by the first measured background intensity, resulting in a corrected background intensity, which is used in a corrected FP measurement equation that is both accurate and precise.

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

DETAILED DESCRIPTION OF THE PRESENTLY PREFERRED EMBODIMENTS

Figure 2:
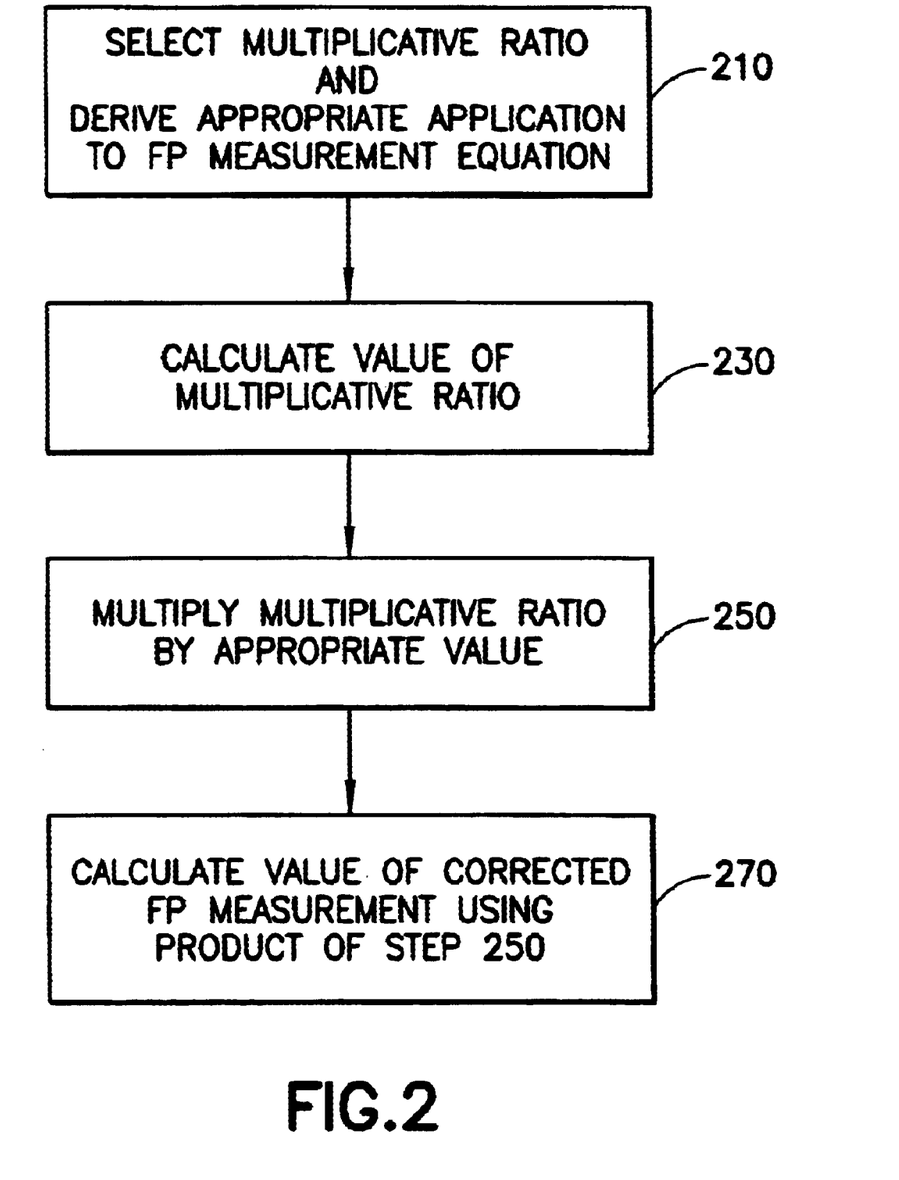
FIG. 2 is an overview of the method according to the presently preferred embodiments of the present invention.

FIG. 2 shows an overview of the method according to embodiments of the present invention. In step 210, an appropriate multiplicative ratio is selected and an appropriate corrected FP measurement equation is determined. The multiplicative ratio is of any two or more actual measured signals, and the particular signals in the ratio are selected in order that their ratio may provide for correcting the effects of background noise on the final FP measurements. This selection may be done by rewriting one of the standard FP measurement equations into a format where ratios are used, or may be done by choosing a term in one of the standard FP measurement equations and determining the ratio most appropriate for eliminating the effects of background noise. The embodiments described below provide examples of each Ad type of selection.

In step 230, the multiplicative ratio is calculated from sample measurements. This step may be performed repeatedly during the testing of a series of microtitre plates, or just a few times, or only once. The number of times the multiplicative ratio is calculated may depend on the measured signals chosen for the multiplicative ratio. For example, if the multiplicative ratio is the ratio of the total background signal to the total signal, this may be calculated once at the beginning of the series. If the multiplicative ratio is the ratio of the total signal of the first sample measured to the total signal of the current sample, it would need to be recalculated for each measurement.

In step 250, the calculated multiplicative ratio is multiplied by an appropriate value in one of the standard FP measurement equations (Equations 1 or 4) or an appropriate value in an equation derived from one of the standard FP measurement equations. After this calculation, the corrected FP measurement is calculated in Step 270. Of course, in a microprocessor, both Steps 250 and 270 may take place roughly simultaneously. This method allows the experimenter to use multiplicative ratios to compensate for background noise, rather than merely subtracting a fixed intensity value. When such multiplicative ratios are applied to the appropriate value or values in an FP measurement equation, the effects of background noise can be reduced without decreasing the precision of the FP measurements.

Such a ratiometric method for dealing with background fluorescence in FP measurements are unknown in the prior art. In fact, the prior art explicitly teaches that ratiometric methods are inappropriate for dealing with background fluorescence ("Ratiometric methods are good at rejecting multiplicative (proportional error) interferences such as absorption, but not additive (constant errors) ones such as background fluorescence," emphasis added, p. 301, *FP/FA Primer*). The prior art teaches that the subtractive approach alone is the best solution to the problem of background fluorescence, even though the subtractive approach results in the degradation of precision.

In one of the presently preferred embodiments of the present invention, the relative proportion of light from a background well fluorescence emission to light from a sample well fluorescence emission is calculated, and is appropriately multiplied into the fluorescence polarization calculation. This new approach, which is described with the equations below, takes measurements of one or more background wells and one or more sample wells, and calculates the ratio of the total background signal to the total signal (BTTR), and the FP of the background wells ($FP_{bkgrnd}$). Then, as samples are measured, FP measurements are made using the conventional uncorrected FP Equation (Equation 2), and then corrected using the method described in detail below. If this method is used, the background correction for the example given in the Background of the Invention would have worked without reducing the instrument signal-to-noise ratio, i.e., without reducing the precision of the measurements. Essentially, the proportion of light from a background well fluorescence emission to light from a sample well fluorescence emission is calculated, and this multiplicative ratio is used to remove the effects of the unwanted background fluorescence, rather than a subtractive approach.

Figure 3:
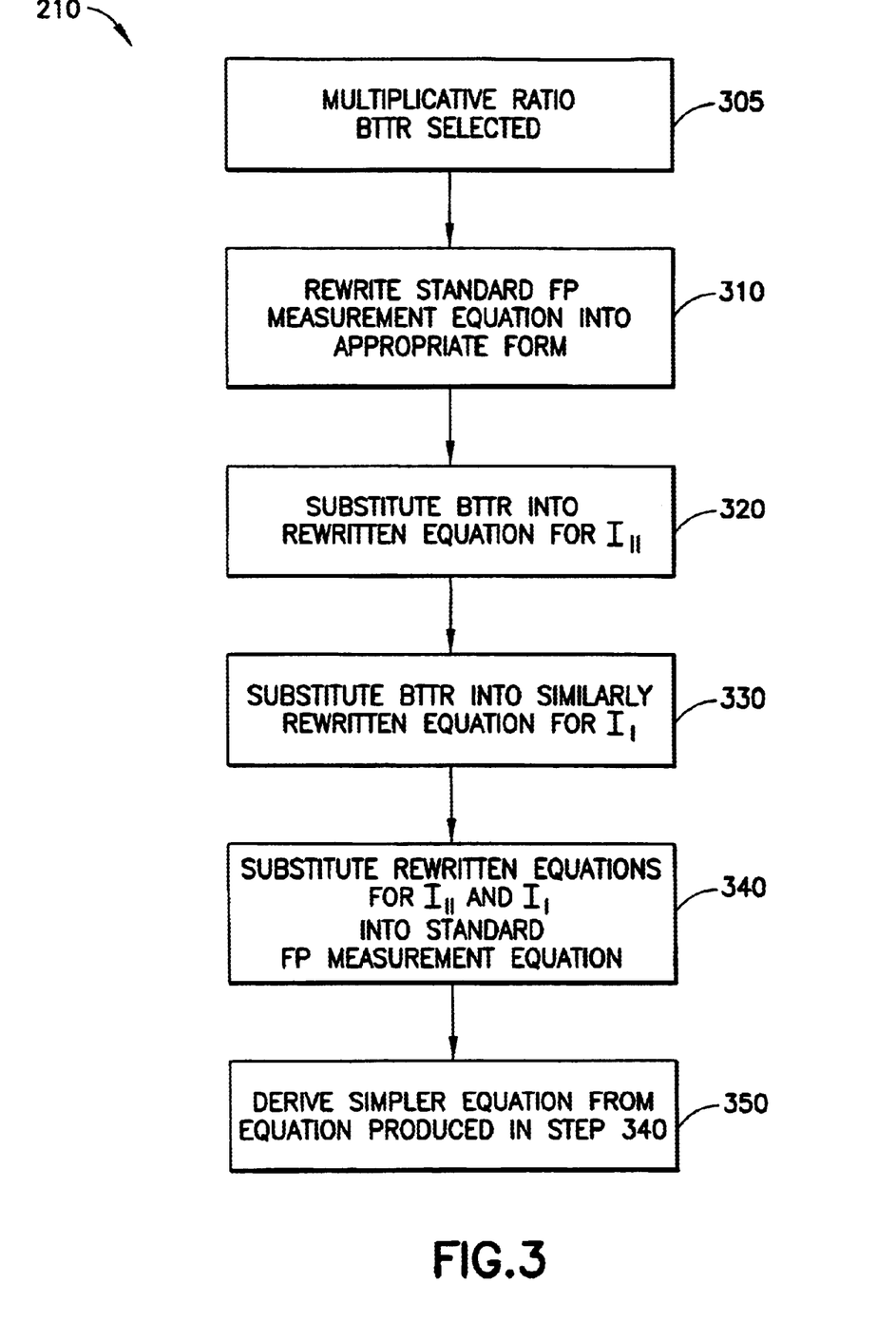
FIG. 3 is a flowchart of the method for selecting a multiplicative ratio and deriving its appropriate application to one of the standard FP measurement equations according to a first presently preferred embodiment of the present invention.

FIG. 3 is a flowchart of the method for selecting a multiplicative ratio and deriving its appropriate application to one of the standard FP measurement equations according to a first presently preferred embodiment of the present invention. In step 305, the multiplicative ratio is assumed. The multiplicative ratio is the ratio of the total background intensity to the total intensity (the intensity of the target sample, the fluorophores, and background), as shown in the following equation:

$$BTTR = \frac{I^{bkgrnd}}{I^{total}} \quad \text{(Equation 5)}$$

This ratio provides a good means to maintain the relative contribution of the background noise in the appropriate proportion to the total intensity of the target substance, fluorophores, and background. Now, we determine the appropriate place in one of the standard FP measurement equations to apply BTTR. There may be more than one place where application of BTTR is appropriate, and experimentation may be used to discover which placement works best. In this case, instead of selecting a total signal value in one of the standard FP measurement equations in order to apply this multiplicative ratio, we rewrite Equation 3 into the following form in Step 310:

$$I_{\parallel}^{corrected} = \frac{I^{total}}{2} * \left(1 + \left(\frac{FP_{meas}}{1000} - \frac{2I_{\parallel}^{bkgrnd}}{I^{total}}\right)\right) \quad \text{(Equation 6)}$$

In Step 320, the final term in Equation 6, $$\frac{2I_{\parallel}^{bkgrnd}}{I^{total}},$$

is rewritten in terms of the multiplicative ratio BTTR and the background fluoresence measurement $FP_{bkgrnd}$ as follows:

$$I_{\parallel}^{corrected} = \frac{I^{total}}{2} * \left(1 + \left(\frac{FP_{meas}}{1000} - BTTR\left(\frac{FP_{bkgrnd}}{1000} + 1\right)\right)\right) \quad \text{(Equation 7)}$$

We now have an equation in which we can take the uncorrected FP measurement $FP_{meas}$, apply BTTR and $PP_{bkgrnd}$, and then calculate a corrected $I_{\parallel}^{corrected}$, which should more closely approximate $I_{\parallel}^{probe}$. Please note that Equations 5 and 7 may be derived in reverse order from how they were derived here. In other words, one might have began with one of the standard FP measurement equations, and then derived an equation where appropriate multiplicative ratios are used. In that case, the appropriate multiplicative ratio would be determined from the derived equation.

In Step 330, an equation similar to Equation 7 is derived for $I_{\perp}^{corrected}$:

$$I_{\perp}^{corrected} = \frac{I^{total}}{2} * \left(1 - \left(\frac{FP_{meas}}{1000} - BTTR\left(\frac{FP^{bkgrnd}}{1000} - 1\right)\right)\right) \quad \text{(Equation 8)}$$

In Step 340, these new corrected intensity values are substituted back into one of the standard FP measurement equations as follows:

$$FP_{corrected} = 1000 * \frac{I_{\parallel}^{corrected} - I_{\perp}^{corrected}}{I_{\parallel}^{corrected} + I_{\perp}^{corrected}} \quad \text{(Equation 9)}$$

Because we seek a method to correctly calculate FP, we take Equation 9 and, in Step 350, we derive a simpler equation by which we may obtain the corrected FP measurement from known values. In the derived equation, one can simply insert the measured $FP_{meas}$ and $FP_{bkgrnd}$ to calculate the corrected $FP_{corrected}$:

$$FP_{corrected} = \frac{FP_{meas} - BTTR * FP_{bkgrnd}}{1 + BTTR} \quad \text{(Equation 10)}$$

Finally, in Equation 10, we have an easy formula by which FP measurements may be corrected without degrading the precision of the measurements. Furthermore, the experimenter may make FP measurements in the conventional manner, and then apply Equation 10 to the conventional FP measurements. To see how well the equation derived using the method of the present invention works, we can apply Equation 10 to the hypothetical measurement made in the Background of the Invention. In the hypothetical, $FP_{meas}$=262 mP and $FP_{bkgrnd}$=450 mP. Applying these values to Equation 10, we obtain a value of $FP_{corrected}$=200 mP, which is exactly equal to our original assumed value of $FP_{probe}$=200 mP.

Figure 4:
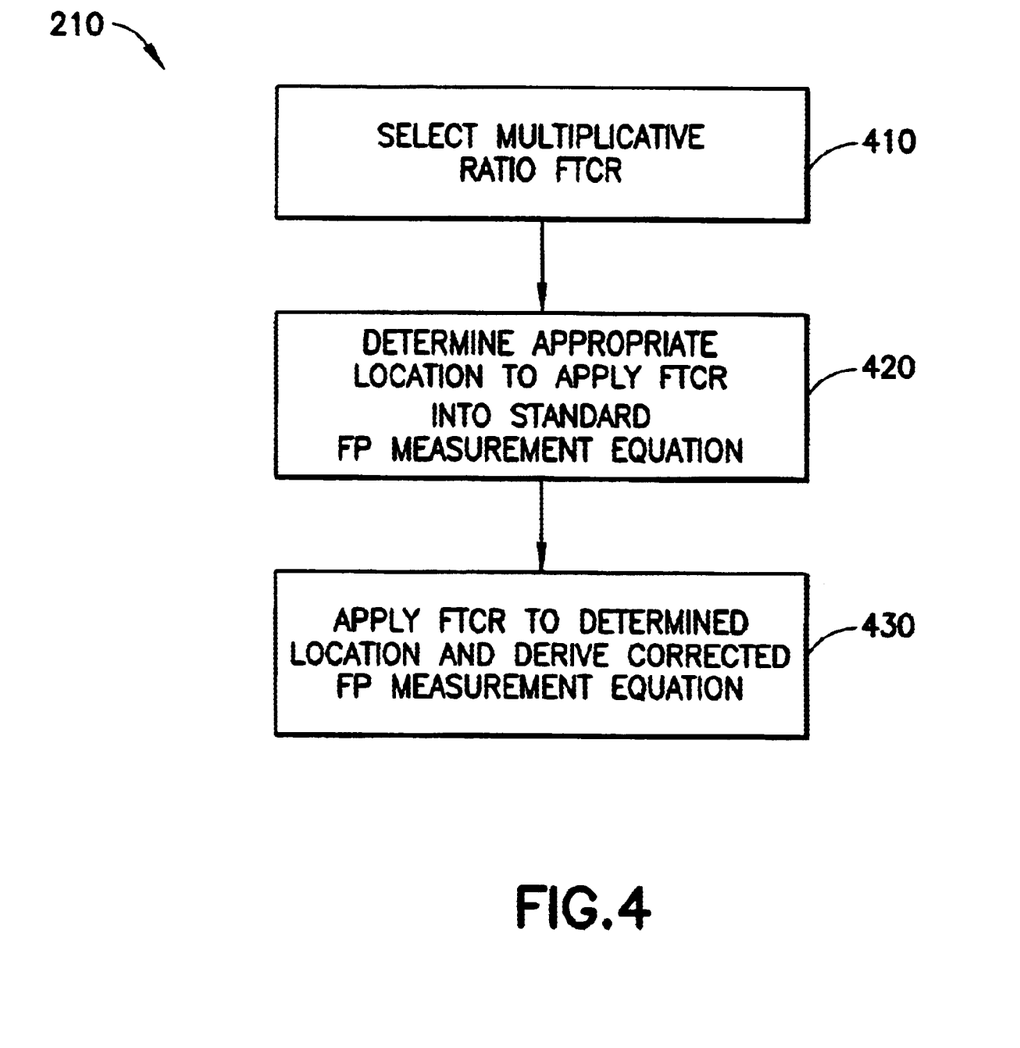
FIG. 4 is a flowchart of the method for selecting a multiplicative ratio and deriving its appropriate application to one of the standard FP measurement equations according to a second presently preferred embodiment of the present invention.

FIG. 4 is a flowchart of the method for selecting a multiplicative ratio and deriving its appropriate application to one of the standard FP measurement equations according to a second presently preferred embodiment of the present invention. In this embodiment of the present invention, the standard FP measurement equation with background correction (Equation 4) is modified by applying a correction factor to the subtracted intensity signals. As shown in FIG. 4, we determine that, since the background intensity may vary from sample to sample but the ratio of the background signal to the total signal may be constant over many samples, we select the following multiplicative ratio in Step 410:

$$FTCR = \frac{I^{first}}{I^{current}} \quad \text{(Equation 11)}$$

where
$I^{first}$=the intensity signal of light from a first sample; and
$I^{current}$=the intensity signal of light from the current sample.

Next, in Step 420, we determine the most appropriate location in one of the standard FP measurements to apply the multiplicative ratio FTCR. We start with Equation 4:

$$FP_{oldcorrection} = 1000 * \frac{(I_{\parallel}^{meas} - I_{\parallel}^{bkgrnd}) - (I_{\perp}^{meas} - I_{\perp}^{bkgrnd})}{(I_{\parallel}^{meas} - I_{\parallel}^{bkgrnd}) + (I_{\perp}^{meas} - I_{\perp}^{bkgrnd})} \quad \text{(Equation 4)}$$

We assume that, when using Equation 4, the background intensities $I_{\parallel}^{bkgrnd}$ and $I_{\perp}^{bkgrnd}$ are taken once at the beginning of the series of microtitre plates. Therefore, in order to adjust those two values appropriately for the fluctuations in lamp strength and sample geometry and inhomogeneities, the multiplicative ratio FTCR is applied to those values in the equation as follows in Step 430:

$$FP_{newcorrection} = 1000 * \frac{(I_{\parallel}^{meas} - I_{\parallel}^{bkgrnd} * FTCR) - (I_{\perp}^{meas} - I_{\perp}^{bkgrnd} * FTCR)}{(I_{\parallel}^{meas} - I_{\parallel}^{bkgrnd} * FTCR) + (I_{\perp}^{meas} - I_{\perp}^{bkgrnd} * FTCR)} \quad \text{(Equation 12)}$$

Using this equation, an experimenter can compensate for background fluorescence and for the variations between samples, thus providing a method to achieve both accuracy and precision in the experimenter's FP measurements.

Experimental Verification of the First Embodiment

Figure 5:
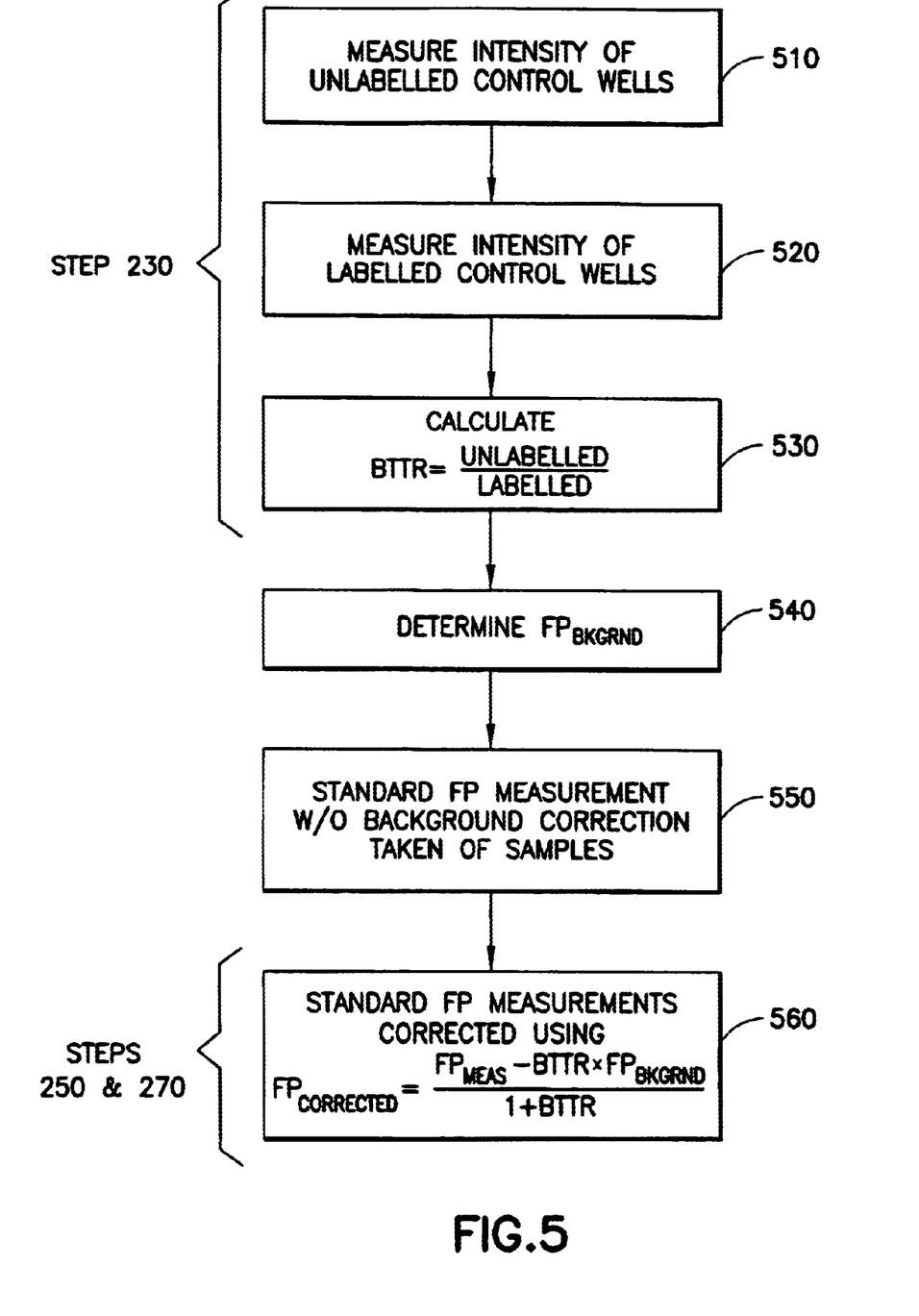
FIG. 5 is a flowchart of a method for making corrected FP measurements using the equation found in the first presently preferred embodiment of the present invention.

The equation derived in the first embodiment (Equation 10) was tested by making corrected FP measurements using the method shown in the flowchart of FIG. 5. For the FP measurements, several assays with known molecular interactions were used, but at label (fluorophore) concentrations well below what is used with conventional instruments. The assay material was from a pharmacogenomics single nucleotide polymorphism (SNP) experiment designed to give a high FP value when the target SNP allele is present to match the template, in this case a T allele.

On a Symmetry FP Plate Reader prototype (this type of FP Plate Reader is now called Affinity) from Cambridge Research & Instrumentation (Cambridge, Mass.), a row of control wells were measured simultaneously by the Symmetry (Affinity) CCD camera. The left half of the row was filled with all assay materials except the fluorescence label, and the right half was filled with the typical assay mix, including the fluorescence label. In Step 510 of FIG. 5, the total signal from the left half (unlabelled) of the row of wells is measured. In Step 520, the total signal from the right half (labelled) of the row of wells is measured. The background-to-total-ratio (BTTR) is calculated in Step 530 by dividing the total unlabelled signal of Step 510 by the total labelled signal of Step 520. In Step 540, the background fluorescence polarization ($FP_{bkgrnd}$) is determined. In this case, the background fluorescence polarization was determined using the Symmetry (Affinity) FP equation (as defined in "Fluorescence Polarization Assay System and Method", U.S. patent application Ser. No. 09/395,661, assigned to the same assignee as the present application and hereby incorporated by reference) on the intensity signal from the right half wells.

In Step 550, the series of microtitre plates containing samples were processed, and the standard FP measurement without background correction (Equation 3) was made. Although Step 550 is performed here after Steps 510–540, Step 550 could have been performed before Steps 510–540. Furthermore, Steps 510–540 only occur once here, at the beginning of the series of samples; however, these steps could be repeated for each microtitre plate, or every few microtitre plates. After the standard FP measurements are made in Step 550, these standard measurements ($FP_{meas}$) are corrected in Step 560 using the equation derived in the first embodiment:

$$FP_{corrected} = \frac{FP_{meas} - BTTR * FP_{bkgrnd}}{1 + BTTR} \quad \text{(Equation 10)}$$

Now that the FP measurements have been corrected according to the method of the first embodiment of the present invention, it remains to determine how accurate these readings are. A common way to assess the performance of an FP-based assay is to calculate the signal-to-noise ratio, given as:

$$SNR_{FP} = \frac{FP_{bound} - FP_{free}}{STD_{FP}}$$

where $FP_{bound}$ is the fluorescence polarization signal when the fluorophore molecule is bound, $FP_{free}$ is the fluorescence polarization signal when it is freely spinning, and $STD_{FP}$ is the standard deviation of the FP signal taken over multiple replicates of the sample under study.

For this test, the STD was averaged over all four alleles. The results of the experiments, which used eight different solutions (4 ROX with varying sample quantities; and 4 TAMRA with varying sample quantities), for the Symmetry (Affinity) FP Plate Reader using the background correction scheme are given below in Table 1.

TABLE 1

Symmetry (Affinity) FP Plate Reader using ratiometric background correction algorithm

| Experiment | T | A | C | G | ave. STD | SNR |
|---|---|---|---|---|---|---|
| ROX, 12.5 | 376.1 | 88.1 | 93.4 | 74.9 | 1.7 | 167.7 |
| ROX, 1.25 | 316.1 | 84.0 | 87.9 | 75.0 | 3.0 | 77.3 |
| ROX, 0.25 | 258.6 | 82.5 | 89.8 | 77.6 | 6.1 | 28.6 |
| ROX, 0.12 | 254.1 | 84.4 | 89.1 | 80.8 | 6.3 | 26.8 |
| Tamra, 12. | 329.1 | 99.6 | 99.1 | 82.7 | 2.0 | 117.8 |
| Tamra, 1.2 | 289.0 | 103.3 | 102.1 | 91.3 | 1.4 | 136.2 |
| Tamra, 0.2 | 252.5 | 100.5 | 103.7 | 94.1 | 2.7 | 56.6 |
| Tamra, 0.1 | 262.6 | 96.8 | 102.1 | 96.0 | 4.5 | 36.9 |

In order to show the wide applicability of the inventive method, the same microtitre plates were also read with a Tecan Ultra FP plate reader. This data, which is shown below, illustrates that the ratioimetric approach can also be applied to conventional well-by-well instruments, such as the Tecan Ultra, or the LJL Biosystems Analyst and Aquest, with significant benefit. The data from the Ultra is contained in three tables: Table 2 shows the simple non-corrected FP measurements; Table 3 shows FP measurements with conventional subtractive background compensation; and Table 4 shows FP measurements with the new ratiometric background correction being used.

TABLE 2

Ultra FP Plate Reader w/o any background correction

| Experiment | T | A | C | G | ave. STD | SNR |
|---|---|---|---|---|---|---|
| ROX, 12.5 | 327.5 | 64.5 | 71.5 | 52.5 | 4.9 | 53.5 |
| ROX, 1.25 | 387.0 | 160.0 | 150.0 | 148.5 | 6.9 | 34.0 |
| ROX, 0.25 | 611.0 | 429.5 | 455.0 | 412.5 | 10.6 | 16.8 |
| ROX, 0.12 | 708.5 | 564.5 | 600.0 | 561.5 | 12.6 | 10.6 |
| Tamra, 12. | 288.0 | 62.5 | 60.5 | 43.5 | 1.9 | 119.6 |
| Tamra, 1.2 | 259.5 | 83.0 | 85.0 | 70.0 | 5.8 | 30.9 |
| Tamra, 0.2 | 262.5 | 135.5 | 145.5 | 128.0 | 7.2 | 17.4 |
| Tamra, 0.1 | 277.5 | 179.0 | 180.5 | 190.5 | 3.7 | 25.4 |

TABLE 3

Ultra FP Plate Reader w/conventional background correction

| Experiment | T | A | C | G | ave. STD | SNR |
|---|---|---|---|---|---|---|
| ROX, 12.5 | 317.5 | 53.7 | 56.5 | 36.4 | 3.7 | 72.1 |
| ROX, 1.25 | 270.0 | 31.6 | 32.2 | 30.0 | 12.2 | 19.6 |
| ROX, 0.25 | 251.7 | 50.1 | 44.0 | 8.7 | 27.1 | 7.8 |
| ROX, 0.12 | 152.5 | −70.5 | −26.6 | −66.0 | 47.6 | 4.3 |
| Tamra, 12. | 284.3 | 57.8 | 55.0 | 38.1 | 2.5 | 94.6 |
| Tamra, 1.2 | 251.5 | 55.7 | 51.7 | 37.2 | 5.1 | 39.8 |
| Tamra, 0.2 | 236.7 | 62.2 | 71.6 | 40.3 | 10.1 | 17.7 |
| Tamra, 0.1 | 212.9 | 46.6 | 56.9 | 47.4 | 21.9 | 7.4 |

TABLE 4

Ultra FP Plate Reader using ratiometric background correction algorithm

| Experiment | T | A | C | G | ave STD | SNR |
|---|---|---|---|---|---|---|
| ROX, 12.5 | 319.3 | 52.8 | 56.2 | 36.8 | 4.3 | 63.4 |
| ROX, 1.25 | 296.4 | 30.4 | 34.7 | 28.0 | 12.1 | 21.9 |
| ROX, 0.25 | 380.5 | 39.5 | 70.0 | 15.1 | 13.8 | 24.6 |
| ROX, 0.12 | 392.2 | −29.9 | 52.1 | −63.9 | 13.3 | 30.5 |
| Tamra, 12. | 284.1 | 57.6 | 55.0 | 38.6 | 2.4 | 97.3 |
| Tamra, 1.2 | 251.1 | 56.4 | 55.0 | 37.9 | 4.7 | 42.9 |
| Tamra, 0.2 | 233.3 | 50.1 | 65.6 | 33.1 | 8.1 | 22.8 |
| Tamra, 0.1 | 229.5 | 38.2 | 58.5 | 43.0 | 9.6 | 19.1 |

In each case, the figure of merit is the signal-to-noise ratio (SNR) in the right-most column. Note that the Ultra data gets significantly better at the low label concentrations when the new ratiometric approach is used, compared to when the conventional approach is used. For example, the SNR for ROX 0.25 and ROX 0.12 using the background correction algorithm according to the first embodiment of the present invention are 24.6 and 30.5, respectively, in comparison with the extremely poor 7.8 and 4.3, respectively, for the same FP Plate Reader using the conventional background correction scheme.

It is also noteworthy that, with the Symmetry (Affinity) FP Plate Reader data, the accuracy across a 100-fold dilution is extremely high, even though the magnitude of the background fluorescence is a substantial fraction of the total signal (up to 25%) at the 125 pM tracer concentration. This suggests that the new background correction algorithm derived according to the first embodiment of the present invention, when used with the Symmetry (Affinity) FP Plate Reader and the Symmetry (Affinity) FP equation (as defined in "Fluorescence Polarization Assay System and Method", U.S. patent application Ser. No. 09/395,661, mentioned and incorporated above), provides a means to push the label concentrations well below 100 pM and still obtain adequate signal-to-noise ratios for a robust assay.

There is an additional advantage in using a ratiometric approach to background correction. In the prior art, when wide variations in FP measurements are presented to the experimenter, she can not tell whether there is something wrong with the experiment (e.g., some samples are corrupted) or the variations are caused by calculation drift due to the error noise introduced by background correction. This can lead to a lengthy experiment being performed before the fact that the experiment has a problem is detected, thus wasting time and effort. By contrast, when an experimenter notices wide variations between FP measurements using the present invention, it is clear there is a problem with the experiment itself.

As is known to those skilled in the art, FP measurements and FA (Fluorescence Anistrophy) measurements are intimately related, as they both depend on intensity ratios. In fact, both FP and FA equations involve the same intensity measurements and contain the same information. Therefore, the method according to the present invention may be applied to FA measurements as well as FP measurements. For example, consider the following FA measurement equation using the prior art subtractive approach to compensate for background fluorescence:

$$FA_{oldcorrection} = 1000 * \frac{(I_{\parallel}^{meas} - I_{\parallel}^{bkgrnd}) - (I_{\perp}^{meas} - I_{\perp}^{bkgrnd})}{(I_{\parallel}^{meas} - I_{\parallel}^{bkgrnd}) + 2*(I_{\perp}^{meas} - I_{\perp}^{bkgrnd})} \quad \text{(Equation 13)}$$

The method according to the second embodiment of the present invention may be applied to the above equation, resulting in:

$$FP_{newcorrection} = 1000 * \frac{(I_{\parallel}^{meas} - I_{\parallel}^{bkgrnd} * FTCR) - (I_{\perp}^{meas} - I_{\perp}^{bkgrnd} * FTCR)}{(I_{\parallel}^{meas} - I_{\parallel}^{bkgrnd} * FTCR) + 2*(I_{\perp}^{meas} - I_{\perp}^{bkgrnd} * FTCR)} \quad \text{(Equation 14)}$$

Thus, the method according to the present invention may be applied to FA measurement equations to compensate for background fluorescence while maintaining both precision and accuracy.

While there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A method for correcting for background fluorescence in one of a fluorescence polarization and a fluorescence anistrophy (FP/FA) measurement of a sample, comprising the steps of:

taking an initial FP/FA measurement of a sample, wherein the initial FP/FA measurement is uncorrected for background fluorescence;

calculating a ratio of an intensity of a background fluorescence to an intensity of a sample fluorescence (BTTR), wherein the sample fluorescence comprises at least a label fluorescence;

determining a FP/FA measurement of a background; and calculating a corrected FP/FA measurement using the calculated BTTR and the determined FP/FA of the background.

2. The method of claim 1, wherein the FP/FA measurement is an FP measurement, and the step of calculating a corrected FP measurement comprises the step of:

calculating a corrected fluorescence polarization measurement ($FP_{corrected}$) by using the following equation:

$$FP_{corrected} = \frac{FP_{meas} - BTTR * FP_{bkgrnd}}{1 + BTTR};$$

wherein $FP_{meas}$=the initial FP measurement taken of the sample;

$FP_{bkgrnd}$=the determined FP measurement of the background.

3. The method of claim 1, wherein FP/FA measurements are being taken of a plurality of samples, and the step of calculating the BTTR comprises the steps of:

measuring an intensity of a plurality of wells containing samples in a microtitre plate, wherein each of the samples comprise an assay of at least a target substance and fluorophores;

measuring an intensity of a plurality of background wells in a microtitre plate, wherein each background well contains one or more assay components other than the fluorophores; and dividing the measured intensity of the background wells by the measured intensity of the sample wells.

4. The method of claim 1, wherein the sample comprises an assay of at least a target substance and fluorophores, and the step of determining a FP/FA measurement of a background comprises the steps of:

measuring an intensity of parallel polarized light ($I_\parallel^{bkgrnd}$) from at least one well containing one or more assay components other than the fluorophores;

measuring an intensity of perpendicularly polarized light ($I_\perp^{bkgrnd}$) from the at least one well containing one or more assay components other than the fluorophores; and calculating the FP/FA measurement of the background using the measured intensity of parallel polarized light ($I_\parallel^{bkgrnd}$) and the measured intensity of perpendicularly polarized light ($I_\perp^{bkgrnd}$).

5. The method of claim 1, wherein a fluorophore concentration of an assay of the sample is at a low level.

6. The method of claim 1, wherein a fluorophore concentration of an assay of the sample is near the $K_d$ point.

7. A method for correcting for background fluorescence in one of a fluorescence polarization and a fluorescence anistrophy (FP/FA) measurement of a plurality of samples, wherein each of the plural samples comprise an assay of at least a target substance and fluorophores, comprising the steps of:

measuring an intensity of parallel polarized light ($I_\parallel^{bkgrnd}$) from at least one well containing one or more assay components other than the fluorophores;

measuring an intensity of perpendicularly polarized light ($I_\perp^{bkgrnd}$) from the at least one well containing one or more assay components other than the fluorophores;

measuring a first sample intensity of a fluorescence of a first sample;

measuring a current sample intensity of a fluorescence of a current sample;

calculating a ratio of the measured first sample intensity to the measured current sample intensity (FTCR);

measuring an intensity of parallel polarized light ($I_\parallel^{crrnt}$) from the current sample;

measuring an intensity of perpendicularly polarized light ($I_\perp^{crrnt}$) from the current sample; and one of:

calculating a corrected FH measurement ($FP_{corrected}$) using following equation:

$$FP_{corrected} = 1000 * \frac{(I_\parallel^{crrnt} - I_\parallel^{bkgrnd} * FTCR) - (I_\perp^{crrnt} - I_\perp^{bkgrnd} * FTCR)}{(I_\parallel^{crrnt} - I_\parallel^{bkgrnd} * FTCR) + (I_\perp^{crrnt} - I_\perp^{bkgrnd} * FTCR)}; \text{ and}$$

calculating a corrected FA measurement ($FA_{corrected}$) using the following equation:

$$FA_{corrected} = 1000 * \frac{(I_\parallel^{crrnt} - I_\parallel^{bkgrnd} * FTCR) - (I_\perp^{crrnt} - I_\perp^{bkgrnd} * FTCR)}{(I_\parallel^{crrnt} - I_\parallel^{bkgrnd} * FTCR) + 2*(I_\perp^{crrnt} - I_\perp^{bkgrnd} * FTCR)}.$$

8. The method of claim 7, wherein a tracer concentration of an assay of the sample is at a low level.

9. A method for correcting for background fluorescence in one of a fluorescence polarization and a fluorescence anistrophy (FP/FA) measurement of a sample, comprising the steps of:

calculating a value of a multiplicative ratio using measurements from at least one sample, wherein the multiplicative ratio is of at least two values, wherein the at least two values are from the group comprising an intensity of a background fluorescence and an intensity of a sample fluorescence;

applying the calculated value of the multiplicative ratio to a corrected FP/FA measurement equation in which the multiplicative ratio is a term; and calculating a corrected FP/FA measurement using the corrected FP/FA measurement equation.

10. The method of claim 9, further comprising the steps of:

selecting the multiplicative ratio; and determining the corrected FP/FA measurement equation in which the selected multiplicative ratio is a term.

11. The method of claim 10, wherein both the step of determining the corrected FP/FA measurement equation and the step of selecting the multiplicative ratio are performed at the same time, the combined steps comprising the step of:

rewriting a standard FP/FA measurement equation in order to derive an FP/FA measurement equation in which at least one term is a multiplicative ratio of at least two values, wherein the at least two values are from the group comprising an intensity of a background fluorescence and an intensity of a sample fluorescence.

12. The method of claim 9, wherein the multiplicative ratio is a ratio of an intensity of a background fluorescence to an intensity of a sample fluorescence (BTTR), wherein the sample fluorescence comprises at least a label fluorescence.

13. The method of claim 12, wherein the FP/FA measurement is an FP measurement, further comprising the steps of:

taking an initial FP measurement ($FP_{meas}$) using a standard uncorrected FP measurement equation; and determining an FP measurement of a background ($FP_{bkgrnd}$);

wherein the corrected FP measurement ($FP_{corrected}$) equation comprises:

$$FP_{corrected} = \frac{FP_{meas} - BTTR * FP_{bkgrnd}}{1 + BTTR}.$$

14. The method of claim 9, wherein FP/FA measurements are being taken of a plurality of samples.

15. The method of claim 9, wherein the multiplicative ratio is a ratio of a first sample intensity of a first sample fluorescence to a current sample intensity of a current sample fluorescence (FTCR).

16. The method for correcting background fluorescence of claim 15, wherein the FP/FA measurement is an FP measurement and the sample comprises an assay of at least a target substance and fluorophores, and the step of calculating a corrected FP measurement ($FP_{corrected}$) uses the following equation:

$$FP_{corrected} = 1000 * \frac{(I_{\|}^{crmt} - I_{\|}^{bkgrnd} * FTCR) - (I_{\perp}^{crmt} - I_{\perp}^{bkgrnd} * FTCR)}{(I_{\|}^{crmt} - I_{\|}^{bkgrnd} * FTCR) + (I_{\perp}^{crmt} - I_{\perp}^{bkgrnd} * FTCR)};$$

wherein
- $I_{\|}^{crmt}$=the measured intensity of parallel polarized light from a current sample;
- $I_{\perp}^{crmt}$=the measured intensity of perpendicularly polarized light from a current sample;
- $I_{\|}^{bkgrnd}$=the intensity of parallel polarized light from at least one well containing one or more assay components other than the fluorophores; and
- $I_{\perp}^{bkgrnd}$=the intensity of perpendicularly polarized light from the at least one well containing one or more assay components other than the fluorophores.

17. The method for correcting background fluorescence of claim 15, wherein the FP/FA measurement is an FA measurement and the sample comprises an assay of at least a target substance and fluorophores, and the step of calculating a corrected FA measurement ($FA_{corrected}$) uses the following equation:

$$FA_{corrected} = 1000 * \frac{(I_{\|}^{crmt} - I_{\|}^{bkgrnd} * FTCR) - (I_{\perp}^{crmt} - I_{\perp}^{bkgrnd} * FTCR)}{(I_{\|}^{crmt} - I_{\|}^{bkgrnd} * FTCR) + 2 * (I_{\perp}^{crmt} - I_{\perp}^{bkgrnd} * FTCR)};$$

wherein
- $I_{\|}^{crmt}$=the measured intensity of parallel polarized light from a current sample;
- $I_{\perp}^{crmt}$=the measured intensity of perpendicularly polarized light from a current sample;
- $I_{\|}^{bkgrnd}$=the intensity of parallel polarized light from at least one well containing one or more assay components other than the fluorophores; and
- $I_{\perp}^{bkgrnd}$=the intensity of perpendicularly polarized light from the at least one well containing one or more assay components other than the fluorophores.

18. The method of claim 9, wherein a fluorophore concentration of an assay of the sample is at a low level.

19. The method of claim 9, wherein a fluorophore concentration of an assay of the sample is near the $K_d$ point.

* * * * *